United States Patent [19]

Kung et al.

[11] Patent Number: 5,736,344
[45] Date of Patent: *Apr. 7, 1998

[54] SERUM PYRIDINIUM CROSSLINKS ASSAY

[75] Inventors: Viola T. Kung, Menlo Park; Baltazar Gomez, Jr., Fremont, both of Calif.

[73] Assignee: Metra Biosystems, Inc., Mountain View, Calif.

[*] Notice: The term of this patent shall not extend beyond the expiration date of Pat. No. 5,527,715.

[21] Appl. No.: 482,109

[22] Filed: Jun. 7, 1995

Related U.S. Application Data

[63] Continuation-in-part of PCT/US93/12321, Dec. 17, 1993, abandoned, which is s continuation-in-part of Ser. No. 140,284, Oct. 20, 1993, abandoned, and a continuation-in-part of Ser. No. 209,924, Mar. 11, 1994, abandoned, which is a continuation-in-part of Ser. No. 992,936, Dec. 17, 1992, abandoned.

[51] Int. Cl.$^6$ .................................................. G01N 33/53
[52] U.S. Cl. .................. 435/7.9; 435/7.1; 435/7.93; 435/7.94; 435/70.21; 435/240.27; 435/975; 435/962; 436/512; 436/518; 436/531; 436/808; 530/387.1; 530/387.9; 530/389.1; 530/391.1; 530/391.3
[58] Field of Search .................. 435/7.1, 7.9, 7.92, 435/7.94, 7.93, 70.21, 240.26, 240.27, 810, 975, 962; 436/512, 518, 530, 531, 86, 87, 161, 808; 530/387.1, 387.9, 389.1, 391.1, 391.3, 391.5, 391.7

[56] References Cited

U.S. PATENT DOCUMENTS

| | | | |
|---|---|---|---|
| 4,973,666 | 11/1990 | Eyre | 530/323 |
| 5,004,806 | 4/1991 | Kung | 530/415 |
| 5,140,103 | 8/1992 | Eyre | 530/327 |
| 5,527,715 | 6/1996 | Kung et al. | 436/547 |
| 5,620,861 | 4/1997 | Cerelli et al. | 435/7.9 |

FOREIGN PATENT DOCUMENTS

| | | |
|---|---|---|
| 0 556152 A1 | 1/1993 | European Pat. Off. |
| WO89/04491 | 5/1989 | WIPO |
| WO89/12824 | 12/1989 | WIPO |
| WO91/08478 | 6/1991 | WIPO |
| WO91/10141 | 7/1991 | WIPO |

OTHER PUBLICATIONS

Steward et al., "The Importance of Antibody Affinity in the Performance of Immunoassays for Antibody," *Journal of Immunological Methods*, vol. 78, pp. 173–190 (1985).

Beardsworth, L.J., et al., "Changes with Age in the Urinary Excretion of Lysyl– and Hydroxylsylpyridinolie, Two New Markers of Bone Collagen Turnover," *J. Bone and Minerals Res.* 5(7):671–676 (1990).

Black, D., et al., "Quatitative Analysis of the Pyridinium Crosslinks of Collagen in Urine Using Ion–Paired Reversed–Phase High–Performance Liquid Chromatography," *Anal. Biochem.* 169:197–203 (1988).

Black, D., et al., "Urinary Excretion of the Hydroxypyridinium Crosslinks of Collagen in Patients with Rheumatoid Arthritis," *Ann. Rheumat. Dis.* 48:641–644 (1989a).

Black, D., et al., "Excretion of Pyridinium Cross–Links in Ovariectomized Rats as Urinary Markers for Increased Bone Resorption," *Calcif. Tissue Int.* 44:343–347 (1989b).

(List continued on next page.)

*Primary Examiner*—Susan Wolski
*Attorney, Agent, or Firm*—Peter J. Dehlinger; Vincent M. Powers

[57] ABSTRACT

A method of assaying bone collagen breakdown levels in a human subject useful to screen for the presence of bone resorption disorders. Also disclosed is a method for monitoring the progression and/or treatment response of a cancer condition which involves or has the potential to progress to a metastatic condition which involves abnormalities in bone resorption rates.

20 Claims, 3 Drawing Sheets

OTHER PUBLICATIONS

Body, J.J., and Delmas, P.D., "Urinary Pyridinium Cross-Links as Markers of Bone Resorption in Tumor-Associated Hypercalcemia," *J. Clinical Endocrin. and Metab.* 74:471–475 (1992).

Coleman, R.E., et al., "Preliminary Results of the Use of Urinary Excretion of Pyridinium Crosslinks for monitoring Metastatic Bone Disease," *Br. J. Cancer* 65:766–768 (1992).

Demers, L.M., "New Biochemical Marker for Bone Disease: Is it a Breakthrough?" *Clin. Chem.* 38(11):2169–2170 (1992).

Eyre, D., et al., "Editorial: New Biomarkers of Bone Resorption," *J. Clin. Endocrin. and Metab.* 74(3):470A–470C (1992).

Eyre, D., et al., "Identification of Urinary Peptides Derived from Crosslinking Sites in Bone Collagen in Paget's Disease," *J. Bone & Min. Res.* 3(1):S210, Abstract No. 565 (1988).

Eyre, D.R., et al., "Quantitation of Hydroxypyridinium Crosslinks in Collagen by High-Performance Liquid Chromatography," *Anal. Biochem.* 137:380–388 (1984).

Fujimoto, D., et al., "Isolation and Characterization of a Fluorescent Material in Bovine Achilles Tendon Collagen," *Biochem. & Biophys. Res. Commun.* 76(4):1124–1129 (1977).

Fujimoto, D., et al., "The Structure of Pyridinoline, a Collagen Crosslink," *Biochem. & Biophys. Res. Commun.* 84(1):52–57 (1978).

Fujimoto, D., and Moriguchi, T., "Pyridinoline, a Non-Reducuible Crosslink of Collagen," *J. Biochem.* 83:863–867 (1978).

Fujimoto, D., et al., "Analysis of Pyridinoline, a Cross-Linking Compound of Collagen Fibers, in Human Urine," *J. Biochem.* 94:1133–1136 (1983).

Gunja-Smith, Z., and Boucek, R.J., "Collagen Cross-Linking Compounds in Human Urine," *Biochem. J.* 197:759–762 (1981).

Hanson, D.A., et al., "A Specific Immunoassay for Monitoring Human Bone Resorption: Quatitation of Type I Collagen Cross-Linked N-Telopeptides in Urine," *J. Bone and Mineral Res.* 7(11):1251 (1992).

James, I., et al., "Assay of Pyridinium Crosslinks in Serum Using Narrow-Bone Ion-Paired Reversed Phase High-Performance Liquid Chromatography," *J. Chromatography* 612:41–48 (1993).

Kollerup, G., et al., "Quantitation of Urinary Hydroxypyridinium Cross-Links from Collagen by High-Performance Liquid Chromatography," *Scand. J. Clin. Lab. Invest.* 52:657–662 (1992).

Macek, J., and Adam, M., "Determination of Collagen Degradation Products in Human Urine in Osteoarthrosis," *Z. Rheumatol.* 46:237–240 (1987).

Ogawa, T., et al., "A Novel Fluor in Insoluble Collagen: A Crosslinking Moiety in Collagen Molecule," *Biochem. & Biophys. Res. Commun.* 107(4):1252–1257 (1982).

Ohishi, T., et al., "Quantitative Analyses of Urinary Pyridinoline and Deoxypyridinoline Excretion in Patients with Hyperthyroidism," *Endocrin. Res.* 18(4):281–290 (1992).

Paterson, C.R., et al., "Pyridinium Crosslinks as Markers of Bone Resorption in Patients with Breast Cancer," *Br. J. Cancer* 64:884–886 (1991).

Robins, S.P., "An Enzyme-Linked Immunoassay for the Collagen Cross-Link Pyridinoline," *Biochem. J.* 207:617–620 (1982).

Robins, S.P., "Turnover and Crosslinking of Collagen," in *Collagen in Health and Disease* (Weiss, J.B., et al., Eds.) Churchill Livingston, Edinburgh, Scotland, pp. 160–178 (1982).

Robins, S.P., "Cross-Linking of Collagen," *Biochem. J.* 215:167–173 (1983).

Robins, S.P., and Duncan, A., "Cross-Linking of Collagen," *Biochem. J.* 215:175–182 (1983).

Robins, S.P., et al., "Measurement of the Cross Linking Compound, Pyridinoline, in Urine as an Index of Collagen Degradation in Joint Disease," *Ann. Rheumat. Dis.* 45:969–973 (1986).

Robins, S.P., and Duncan, A., "Pyridinium Crosslinks of Bone Collagen and Their Location in Peptides Isolated from Rat Femur," *Biochim. et Physiophys. Acta* 914:233–239 (1987).

Seibel, M.J., et al., "Urinary Hydroxy-Pyridinium Crosslinks Provide Indices of Cartilage and Bone Involvement in Arthritic Disease," *J. Rheumatol.* 16(7):964–970 (1989).

Seibel, M.J., et al., "Urinary Pyridinium Crosslinks of Collagen: Specific Markers of Bone Resorption in Metabolic Bone Disease," *TEM* 3(7):263 (1992).

Wu, J.-J., and Eyre, D.R., "Identification of Hydroxypyridinium Cross-Linking Sites in Type II Collagen of Bovine Articular Cartilage," *Biochemistry* 23:1850–1857 (1984).

SERUM PYRIDINIUM CROSSLINKS ASSAY

This application is a continuation-in-part of PCT Application No. PCT/US93/12321 filed Dec. 17, 1993, now abandoned, which is a continuation-in-part of U.S. patent application Ser. No. 08/140,284 filed Oct. 20, 1993, now abandoned, and a continuation-in-part of Ser. No. 08/209,924 filed Mar. 11, 1994, now abandoned, which is a continuation-in-part of Ser. No. 07/992,936 filed Dec. 17, 1992, now abandoned.

1. FIELD OF THE INVENTION

The present invention relates to a method for assessing bone collagen breakdown in a human subject, by assaying the level of peptide-free pyridinium crosslinks in a human blood fluid sample.

2. REFERENCES

Black, D., et al., *Anal. Biochem.* 169:197–203 (1988).
Black, D., et al., *Annals of Rheumatic Diseases* 48:641–644 (1989).
Brown, J. P., et al., *Lancet* 1091–1093 (1984).
Campbell, A., Monoclonal Antibody and Immunosensor Technology, Elsevier (1991).
Daniloff, Y., et al., *Connect. Tissue. Res.* 27:187 (1992).
Eyre, D. R., et al., *Anal. Biochem.* 137:380–388 (1984).
Eyre, D. R., et al., *FEBS* 2:337–341 (1987).
Fujimoto, D., et al., *J. Biochem.* 83:863–867 (1978).
Fujimoto, D., et al., *J. Biochem.* 94:167–173 (1983).
Gosling, J., *Clin. Chem.* 36(8):1408 (1990).
Gunja-Smith, Z., et al., *Biochem. J.* 197:759–762 (1981).
Harlow, E., et al., Antibodies: A Laboratory Manual, Cold Spring Harbor Lab (1988).
Henkel, W., et al., *Eur. J. Biochem.* 165:427–436 (1987).
Macek, J., et al., *Z. Rheumatol.* 46:237–240 (1987).
Ogawa, T., et al., *Biochem. Biophys. Res. Commune.* 107:1251–1257 (1982).
Robins, S. P., *Biochem J.* 207:617–620 (1982a).
Robins, S. P., in "Collagen in Health and Disease" (Weiss, J. B., et al., eds.) pp. 160–178, Churchill Livingstone, Edinburgh (1982b).
Robins, S. P., *Biochem. J.* 215:167–173 (1983).
Robins, S. P., et al., *Ann. Rheumatic Dis.* 45:969–973 (1986).
Robins, S. P., et al., *Biochim. Biophys. Acta.* 914:233–239 (1987).
Segel, I., Biochemical Calculations, John Wiley and Sons, (1976).
Seibel, et al., *J. Rheumatol* 16:964–970 (1989).
Wong, S. S., Chemistry of Protein Conjugation and Cross-Linking, CRC Press, Boca Raton, Fla. (1991).

3. BACKGROUND OF THE INVENTION

There are a variety of conditions in humans which are characterized by a high level of bone resorption and by an abnormal balance between bone formation and bone resorption. Among the more common of these are osteoporosis, Paget's disease, and conditions related to the progress of benign and malignant tumors of the bone and metastatic cancers which have been transferred to bone cells from, for example, prostate or breast initial tumors. Other conditions which are associated with changes in collagen metabolism include osteomalacial diseases, rickets, abnormal growth in children, renal osteodystrophy, and a drug-induced osteopenia. Irregularities in bone metabolism are often side effects of thyroid treatments and thyroid conditions per se, such as primary hypothyroidism and thyrotoxicosis as well as Cushing's disease.

It has been recognized that disorders of bone resorption or other conditions characterized by an abnormal balance between bone formation and bone resorption can be detected by altered levels of pyridinium crosslinks in urine (Robins, 1982b; Macek; Black). The crosslinks take the form of compounds containing a central 3-hydroxy pyridinium ring in which the ring nitrogen is derived from the epsilon amino group of lysine or hydroxylysine (Fujimoto, 1978; Robins, 1982a; Gunja-Smith; Ogawa; Eyre).

The pyridinium crosslink compounds found in urine can be grouped into four general classes: (1) native free crosslinks having a molecular weight of about 400 daltons (Fujimoto), (2) glycosylated crosslinks and crosslink peptide forms having a molecular weight of between about 550 and 1,000 daltons (Robins, 1983), (3) crosslink peptide forms having a molecular weight between 1,000 and 3,500 daltons (Robins, 1983, 1984, 1987; Henkel; Eyre), and (4) crosslink peptide forms having a molecular weight greater than 3,500 daltons. In normal adults, these forms account for about 38% (1), 40% (2), 15% (3), and 7% (4) of total urinary crosslinks (Daniloff). About 80% of the free crosslinks in normal adult urine is pyridinoline (or Pyd), whose ring nitrogen is derived from a hydroxylysine residue, and about 20%, deoxypyridinoline, or Dpd, whose ring nitrogen is derived from a lysine residue. This ratio of Pyd/Dpd applies roughly to the other three classes of crosslinks in urine. The higher molecular weight crosslinks can be converted to free crosslinks by acid hydrolysis (Fujimoto, 1978).

Methods for measuring pyridinium crosslinks in urine have been proposed. One of these methods involves the measurement of total hydrolysed Pyd, i.e., Pyd produced by extensive hydrolysis of urinary crosslinks, by quantitating the hydrolysed Pyd peak separated by HPLC (Fujimoto, 1983). The relationship between total hydrolysed Pyd to age was determined by these workers as a ratio to total hydrolysed Pyd/creatinine, where creatinine level is used to normalize crosslink levels to urine concentration and skeletal mass. It was found that this ratio is high in the urine of children, and relatively constant throughout adulthood, increasing slightly in old age. The authors speculate that this may correspond to the loss of bone mass observed in old age.

Studies on the elevated levels of total crosslinks in hydrolyzed urine of patients with rheumatoid arthritis has been suggested as a method to diagnose this disease (Black, 1989). The levels of total hydrolyzed crosslinks for patients with rheumatoid arthritis (expressed as a ratio of total crosslinks measured by HPLC to creatinine) were elevated by a factor of 5 as compared to controls. However, only total hydrolysed Pyd, but not total hydrolysed Dpd, showed a measurable increase.

In a more extensive study using hydrolyzed urines, Seibel et al. showed significant increases in the excretion of bone-specific total hydrolysed Pyd and Dpd crosslinks relative to controls in both rheumatoid and osteoarthritis. The most marked increases for total hydrolysed Pyd were in patients with rheumatoid arthritis (Seibel).

Assay methods, such as those just noted, which involve HPLC quantitation of crosslinks from hydrolysed samples are relatively time-consuming and expensive to carry out, and may not be practical for widespread screening or monitoring therapy in bone-metabolism disorders.

Immunoassays have also been proposed for measuring urinary crosslinks. U.S. Pat. Nos. 4,973,666 and 5,140,103 disclose an assay for measuring bone resorption by detection in urine of certain peptide-linked pyridinium species associated with bone collagen. These are obtained from the urine of patients suffering from Paget's disease, a disease known to involve high rates of bone formation and destruction. The assay relies on immunospecific binding of crosslink compounds containing the specific peptide fragment or extension with an antibody prepared against the crosslink peptide. It is not clear whether and how the concentration of crosslink peptide being assayed relates to total urinary crosslinks.

Robins has described a technique for measuring pyridinoline in urine by the use of an antibody specific to hydrolysed Pyd (Robins, 1986). The method has the limitation that the antibody was found to be specific for the hydrolized form of Pyd, requiring that the urine sample being tested first be treated under hydrolytic conditions. The hydrolytic treatment increases the time and expense of the assay, and precludes measurements of other native pyridinium crosslinks.

PCT International Publication No. WO 91/10141 discloses a method of assessing bone collagen degradation in human subjects by measuring the level of native, peptide-free pyridinoline or deoxypyridinoline in non-hydrolyzed urine samples. The method represents an improvement over earlier methods based on analysis of urine samples because it avoids the hydrolytic sample pretreatment employed previously.

It would be desirable to assay bone collagen degradation levels in a human subject by measuring the level of pyridinium crosslink species in a blood fluid sample. Such an assay could be integrated into an automated clinical system designed to assay a variety of serum analytes. The approach also has the advantage that the measured levels would not have to be corrected for variation in sample volume, e.g., by determining a ratio of deoxypyridinoline/creatinine.

4. SUMMARY OF THE INVENTION

The present invention includes, in one aspect, a method of screening for the presence of a bone resorption disorder in a human subject. In the method, a blood-fluid sample is obtained from a subject and is reacted with an antibody which is capable of reacting immunospecifically with pyridinium crosslinks selected from the group consisting of native free pyridinoline, native free deoxypyridinoline, or both native free pyridinoline and deoxypyridinoline, to form an immunocomplex between the antibody and such pyridinium crosslinks in the sample. The amount of immunocomplex formed is measured to determine the concentration of the selected pyridinium crosslinks in the sample. In one embodiment, the subject is indicated as having such a bone resorption disorder if the determined concentration is above (i) 5 nM native free pyridinoline, (ii) 1 nM native free deoxypyridinoline, or (ii) 6 nM combined native free pyridinoline and deoxypyridinoline. The blood fluid sample may be serum or plasma, for example.

The bone resorption disorders that are screened for by the method include disorders that are characterized by elevated levels of hydrolysed pyridinoline crosslinks in the urine.

The antibody in the method can be a monoclonal antibody or polyclonal antibody, and preferably has a binding constant with respect to the selected pyridinium crosslinks of at least $5 \times 10^7$/molar.

In one embodiment, the antibody used in the method has a ratio of reactivity toward the selected pyridinium crosslinks and urinary pyridinium peptides larger than 1,000 daltons in molecular weight, of greater than about 5:1. In related embodiments, the antibody has a ratio of reactivity toward the selected pyridinium crosslinks and urinary pyridinium peptides larger than 1,000 daltons in molecular weight, of greater than about 10:1, and more preferably, greater than 20:1.

In a specific embodiment, the antibody is specific for native free pyridinoline, and has a ratio of reactivity toward native free pyridinoline and native free deoxypyridinoline of greater than about 5:1. In a second embodiment, the monoclonal antibody is specific for native free deoxypyridinoline, and has a ratio of reactivity toward native free deoxypyridinoline and native free pyridinoline of greater than about 25:1. In another embodiment, the monoclonal antibody is specific for both native free pyridinoline and native free deoxypyridinoline and has a ratio of reactivity toward native free pyridinoline and native free deoxypyridinoline of between about 2:1 and 1:2.

More generally, the ratio of reactivity toward native free pyridinoline and native free deoxypyridinoline can be from greater than 5:1 to less than 1:25, including all ratios in between.

In one preferred embodiment, the sample is contacted, in the presence of the antibody, with a selected pyridinium crosslink-coated solid support effective to compete with such selected crosslinks in the sample for binding to the antibody. The amount of immunocomplex formed between the antibody and the selected pyridinium crosslinks in the sample is measured indirectly, by measuring the amount of antibody bound to the solid support.

In another preferred embodiment, the sample is contacted, in the presence of exogenous reporter-labeled or reporter-labelable selected pyridinium crosslinks, with a solid-phase support that is coated with a selected amount of pyridinium crosslinks, under conditions such that the selected pyridinium crosslinks from the sample compete with the exogenous crosslinks for binding to the immobilized antibody on the support.

The method may be used for monitoring treatment of a condition associated with an elevated level of collagen degradation, by monitoring changes in the concentration of the selected pyridinium crosslinks during such treatment.

In a related aspect, the invention includes a method of monitoring the status of a human cancer which involves or has the potential to progress to a metastatic condition which involves abnormalities in bone resorption rates. In the method, a blood-fluid sample is obtained from a subject and reacted with an antibody capable of reacting immunospecifically with pyridinium crosslinks selected from the group consisting of native free pyridinoline, native free deoxypyridinoline, or both native free pyridinoline and deoxypyridinoline, to form an immunocomplex between the antibody and such pyridinium crosslinks in the sample. The amount of immunocomplex formed is measured to determine the concentration of the selected pyridinium crosslinks in the sample. An abnormality in bone resorption rate associated with the cancer, suggesting possible metastisis in bone, is indicated if the determined pyridinium crosslinks concentration is above (i) 5 nM native free pyridinoline, (ii) 1 nM free deoxypyridinoline, and (ii) 6 nM combined pyridinoline and deoxypyridinoline.

The method may be used for monitoring treatment of a cancer which is characterized by involvement of collagen degradation, by monitoring changes in the selected pyridinium crosslinks concentration during treatment of the cancer.

In another aspect, the invention includes a method of assaying bone collagen breakdown levels in a human subject. In the method, a blood-fluid sample is obtained from a subject and is reacted with an antibody which is capable of reacting immunospecifically with pyridinium crosslinks selected from the group consisting of native free pyridinoline, native free deoxypyridinoline, or both native free pyridinoline and deoxypyridinoline, and where the antibody has a binding constant for said selected crosslinks of at least $10^8$/molar, to form an immunocomplex between the antibody and such pyridinium crosslinks in the sample. The amount of immunocomplex formed is measured to determine the concentration of the selected pyridinium crosslinks in the sample. The subject is indicated as having such a bone resorption disorder if the determined concentration is above (i) 5 nM native free pyridinoline, (ii) 1 nM native free deoxypyridinoline, or (ii) 6 nM combined native free pyridinoline and deoxypyridinoline.

For the methods above, it will be appreciated that lower threshold values can be used in order to increase the likelihood of identifying individuals with elevated levels of bone degradation—for example, for detecting native free pyridinoline, a value of about 3 nM; for native free deoxypyridinoline, a value of about 0.5 nM, and for detecting the combined concentration of native free pyridinoline and deoxypyridinoline, a value of about 3.5 nM.

In another embodiment, the invention includes an antibody having an affinity constant with respect to the above selected pyridinium crosslinks of at least $10^8$/molar. In one embodiment, the antibody has a ratio of reactivity toward the selected pyridinium crosslinks and urinary pyridinium peptides larger than 1,000 daltons in molecular weight, of greater than about 3:1, and preferably greater than about 5:1.

In another aspect, the invention includes a diagnostic kit for use in the methods above. The method includes an antibody such as described above, and detection means for detecting the amount of immunocomplex formed by reaction of the antibody with the selected pyridinium crosslinks from a blood fluid sample.

For detecting native free pyridinoline, the kit for use in the method is preferably effective to detect a blood pyridinoline concentration ("threshold concentration") of at least about 1 nM, and more preferably, at least 0.5 nM. For detecting native free deoxypyridininoline, the kit is preferably effective to detect a blood deoxypyridinoline concentration of at least about 0.1 nM, and more preferably, at least about 0.05 nM. For detecting the combined concentration of pyridinoline and deoxypyridinoline, the threshold concentration is preferably 1.1 nM, and more preferably, 0.6 nM.

In one embodiment, the detection sensitivity of the kit allows detection of the selected pyridinium crosslinks concentration in a selected range, for example, 1–10 nM for pyridinoline, or 0.1–10 nM for deoxypyridinoline.

These and other objects and features of the invention will become more fully apparent when the following detailed description of the invention is read in conjunction with the accompanying drawings.

DETAILED DESCRIPTION OF THE INVENTION

I. Definitions

As used herein, the terms below have the following definitions:

"Pyd" or "pyridinoline" or "free pyridinoline" refers to the crosslink compound shown at I below, where the ring N is derived from the ε amino group of a hydroxylysyl residue, and "Dpd" or "deoxypyridinoline" or "free deoxypyridinoline" refers to the crosslink compound shown at II below, where the ring nitrogen is derived from ε amino group of a lysyl residue.

"Free crosslinks" refers to either compounds I or II or a mixture of the two, i.e., free of any peptide or glycosyl group attachments.

"Glycosylated pyridinoline" or "glyco-Pyd" refers to glycosylated forms of compound I, wherein glycosyl groups are covalently bound to the aliphatic hydroxyl group of Pyd. Two glyco-Pyd crosslinks which have been identified are Gal-Pyd and Glc.Gal-Pyd, which contain the acetals shown at III and IV below, respectively.

"Pyd-peptides" or "pyridinoline-peptides" refers to peptide-derivatized forms of compound I, in which one or more of the three amino acid residues in the compound is linked via a peptide linkage to additional amino acid residues. Similarly, "Dpd-peptides" or "deoxypyridinoline-peptides" refers to peptide-derivatized forms of compound II, in which one or more of the three amino acid residues in the compound is linked via a peptide linkage to additional amino acid residues.

"Pyridinium-peptides" refers to a mixture of Pyd-peptides and Dpd-peptides.

"Pyd-peptides having a molecular weight greater than 1000 daltons" or "Pyd-peptides (MW>1000)" refers to Pyd-peptides retained by a dialysis membrane having a 1,000 molecular weight cutoff.

"Pyd crosslinks" refers to the pyridinium crosslinks which contain compound I either in free or peptide-derivatized form. Pyd crosslinks include Pyd, glyco-Pyd and Pyd-peptides. Similarly, "Dpd crosslinks" refers to the pyridinium crosslinks which contain compound II either in free or peptide-derivatized form. "Dpd crosslinks" include Dpd and Dpd-peptides.

"Pyridinium crosslinks" refers to pyridinium crosslinks which contain compounds I and/or II in free and/or peptide-linked form.

"Total Pyd" or "T-Pyd" refers to total hydrolysed Pyd produced by hydrolyzing Pyd crosslinks to Pyd. Similarly, "Total Dpd" or "T-Dpd" refers to total hydrolysed Dpd produced by hydrolyzing Dpd crosslinks to Dpd.

"Hydrolysed-Pyd" of "H-Pyd" refers to Pyd produced by hydrolysing Pyd crosslinks in 6N HCl at 110° C. for 16 hours. Similarly, "Hydrolysed-Dpd" of "H-Dpd" refers to Dpd produced by hydrolysing Dpd crosslinks in 6N HCl at 110° C. for 16 hours.

"Native Pyd" of "N-Pyd" refers to Pyd which has not been subjected to hydrolytic conditions. Similarly, "Native Dpd" of "N-Dpd" refers to Dpd which has not been subjected to hydrolytic conditions.

"Native free" or "native, peptide-free" refers to a pyridinium compound having structure I or II (or both) shown above, and which has not been subjected to hydrolytic conditions.

"Blood fluid" refers to cell-free fluid and fractions thereof, obtained from blood, e.g., serum or plasma.

"Limit of detection" refers to a concentration of the selected pyridinium crosslinks that can be distinguished from a negative sample (i.e., a sample lacking the selected pyridinium crosslinks). More specifically, the limit of detection is the selected concentration of the selected pyridinium crosslinks which gives rise to a signal that is different by at least two standard deviations from the signal observed for a negative sample. Thus a limit of detection of native free deoxypyridinoline of about 0.05 nM implies the ability to detect concentrations of native free deoxypyridinoline of at least 0.05 nM. The actual limit of detection may be lower than the specified limit, e.g., in the present example, an assay with a specified limit of detection of 0.05 nM may have an actual limit of detection of 0.02 nM.

"Detection sensitivity" refers to the range of analyte concentrations which can be reliably measured in a given assay procedure. Thus, a detection sensitivity which allows detection of native free pyridinoline concentrations in the range 0.1–10 nM means that the assay procedure can detect concentrations of analyte of 0.1 nM, and can detect differences in the analyte concentration in the range 0.1–10 nM. The actual range of detection for the assay may be broader than the specified range, e.g., in the present example, an assay method having a detection sensitivity in the range 0.1–10 nM may be able to detect and distinguish analyte concentrations in the range 0.05–20 nM.

II. Preparation of Antibody Reagent

This section describes the production of monoclonal and polyclonal antibodies ("antibody reagent") which are specific for selected native free pyridinium crosslinks (either N-Pyd, N-Dpd, or both). In one embodiment, the antibodies have a ratio of reactivity toward the selected native free pyridinium crosslink and urinary pyridinium peptides larger than 1,000 daltons in molecular weight, of greater than about 3:1, and preferably greater than about 5:1.

In a specific embodiment, where the antibody is for binding native free pyridinoline, the antibody preferably has a ratio of reactivity toward native free pyridinoline and native free deoxypyridinoline of greater than about 5:1, preferably greater than about 20:1, and more preferably greater than about 100:1.

In another specific embodiment, where the antibody is for binding native free deoxypyridinoline, the antibody preferably has a ratio of reactivity toward native free deoxypyridinoline and native free pyridinoline of greater than about 5:1, preferably greater than about 25:1, and more preferably greater than about 100:1.

In a third specific embodiment, where the antibody is for binding both native free pyridinoline and native free deoxypyridinoline, the antibody preferably has a ratio of reactivity toward native free pyridinoline and native free deoxypyridinoline of between about 2:1 and 1:2.

The antibody reagent of the invention preferably has a binding affinity constant for the selected pyridinium species (N-Pyd or N-Dpd) of greater than about $5 \times 10^7$/molar.

A. Immunogen

The immunogen used in producing the antibody reagent is Dpd or Pyd conjugated to a carrier molecule, typically a carrier protein such as keyhole limpet hemocyanin (KLH).

The Pyd can be native Pyd (N-Pyd) or hydrolyzed Pyd (H-Pyd). Likewise, the Dpd can be native Dpd (N-Dpd) or hydrolyzed Dpd (H-Dpd). For obtaining N-Dpd or N-Pyd, gross separation of N-Dpd or N-Pyd from other pyridinium compounds in urine can be achieved by fractionation of urine, as described in Example 2. Briefly, a concentrate of urine is applied to a Sephadex G-10 column, and the total pyridinium-containing fractions are eluted. The eluate is then applied to a column of phosphocellulose equilibrated with sodium citrate, and eluted with salt, yielding free crosslinks in a single peak. As the sample is not subjected to hydrolysis conditions, the peak contains not only the N-Dpd and N-Pyd forms ("free crosslinks"), but also glyco-Pyd, including Gal-Pyd and Glc-Gal-Pyd as described above. Further purification is then conveniently conducted by standard methods, for example, using ion exchange on sulfonated polystyrene beads, or HPLC. Typical protocols for this separation are found, for example, in Black, et al., 1988, Seibel, et al., 1989, and detailed in Example 2.

Alternatively, hydrolyzed Pyd or Dpd can be produced by acid hydrolysis of pyridinium crosslinks in bone collagen or urine, purified as described in Black et al., 1988, for example.

Coupling of Pyd or Dpd to a carrier protein is by standard coupling methods, typically using a bifunctional coupling agent which forms, at one coupling end, an amide linkage to one of the free carboxyl groups of Pyd or Dpd, and at the other coupling end an amide or ester or disulfide linkage to the carrier protein, according to standard methods.

Alternatively, in a preferred embodiment, the Pyd or Dpd can be directly coupled to the protein, e.g., in the presence of a water-soluble carboxyl activating agent such as EDC (1-(3-dimethylaminopropyl)-3-ethylcarbodiimide), also according to well known methods. The latter approach is illustrated in Example 3, which describes the coupling of Dpd to keyhole limpet hemocyanin (KLH) by EDC activation. General coupling reactions for derivatizing a carrier protein with a peptide antigen are given in Harlow (1988), pp. 77–87, and in Wong (1991).

B. Monoclonal Antibody Reagent

To prepare a monoclonal antibody reagent, the immunogen described above is used to immunize an animal, such as a mouse, from which antigen-specific lymphocytes can be obtained for immortalization. One animal that has been found suitable is the "autoimmune" MRL/MpJ-lpr mouse available from Jackson Laboratory (Bar Harbor, Minn.).

Where an antibody which is specific for N-Pyd is desired, a Pyd-immunogen is typically used. Likewise, where an antibody which is specific for N-Dpd is desired, a Dpd-immunogen is typically used. An antibody which recognizes both Pyd and Dpd may be obtained using a Pyd-immunogen or a Dpd-immunogen.

B.1 N-Pyd Monoclonal Antibody.

For producing a monoclonal antibody reagent which is specific for N-Pyd, mice can be immunized using a series of injections of H-Pyd-KLH immunogen, as outlined in Example 4. About 8 weeks after initial immunization, spleen cells are harvested and fused with a P3X63Ag8.653 myeloma cell line. Selection for successful fusion products can be performed in HAT in conditioned S-DMEM medium, according to published methods (see, generally, Harlow, pp. 196–212). Successful fusion products are then screened for immunoreactivity with N-Pyd, using a competitive immunoassay format similar to that described in Example 8. Cell lines which show high affinity binding to N-Pyd are subcloned by limiting dilution and further screened for production of antibodies with high binding affinity for N-Pyd. One subcloned cell line obtained by the procedure above and which gave high antibody affinity for N-Pyd is designated herein as Mab-XXV-3G6-3B11-1A10. Samples of this cell line have been deposited with the American Type Culture Collection, 12301 Parklawn Dr., Rockville, Md. 20852), and have been assigned ATCC No. HB11089.

To produce the antibody reagent, the hybridoma cell line is grown in a suitable medium (Harlow, pp. 247–270), such as Dulbecco's modified Eagle's medium (DMEM) supplemented as described in the Materials and Methods section below. Monoclonal antibodies ("Mabs") are harvested from the medium and can be concentrated and stored according to published methods (Harlow pp. 271–318).

As noted above, an important feature of the present invention is the specificity of the antibody reagent for N-Dpd and N-Pyd relative to larger molecular weight pyridinium crosslinks in urine. The relative specificity of the antibody reagent for N-Pyd, N-Dpd, and other urinary pyridinium crosslinks can be determined by a competitive binding assays for N-Pyd, as detailed in Example 10.

Briefly, various purified crosslink samples, including N-Pyd and N-Dpd, as well as an amino acid mixture containing the 20 common amino acids in equimolar amounts (150 µM each), are reacted with a limiting amount of the antibody reagent over a solid-phase support having attached N-Pyd under conditions in which the pyridinium crosslinks in the sample compete with the support-bound N-Pyd for binding to the antibody. The extent of binding of antibody to the solid-support provides a measure of the relative reactivities of the sample crosslinks for the antibody reagent.

In accordance with the procedure outlined in Example 10, the levels of binding of N-Pyd, N-Dpd, Pyd-peptides (MW>1,000), and an amino acid mixture (150 µM each of the common 20 amino acids), to monoclonal antibodies from cell line Pyd XXV-3G6-3B11-1A10 were examined. The apparent Pyd concentration of each sample was determined using standard curves established using purified N-Pyd. The percent reactivity of each sample was calculated as a ratio of apparent concentration (measured using the N-Pyd standard curve above) to total Pyd crosslink concentration in the sample determined by HPLC for total H-Pyd (times 100), or to total Dpd-crosslink concentration as determined by HPLC for total H-Dpd (times 100) in the case of the N-Dpd sample. The results are shown in Table 1, where reactivity with N-Pyd has been defined as 100%.

TABLE 1

| Cross-Reactivity of N-Pyd Monoclonal Antibody | |
| --- | --- |
| N-Pyd | 100% |
| N-Dpd | 16% |
| Pyd-Peptide (>1000) | <1% |
| Amino Acid Mixture (150 µM) | <1% |

As seen, the monoclonal antibody reagent is highly selective for N-Pyd relative to N-Dpd, showing a ratio of reactivity toward native free pyridinoline and native free deoxypyridinoline that is greater than about 3:1, and in the present case, greater than 5:1. The reagent is also selective for N-Pyd over the pyridinium-peptide forms tested (quantitated for total Pyd content), showing a ratio of reactivity toward pyridinoline peptides larger than 1,000 daltons in molecular weight, of greater than about 100:1. In addition, the reagent shows minimal cross reactivity (<1%) with the amino acid mixture tested.

More generally, the Mab reagent which is specific for N-Pyd has a reactivity toward native free pyridinoline (N-Pyd) and Pyd-peptides (MW>1000), of greater than 5:1, preferably greater than 10:1, more preferably greater than 25:1, and in the present case, greater than 100:1, as measured by the above assay.

B.2 N-Dpd Monoclonal Antibody.

For producing a monoclonal antibody reagent which is specific for N-Dpd, the above procedure for obtaining N-Pyd Mabs can be used, except that Dpd-KLH is used as immunogen, and immunoreactivity screening is done with an assay for N-Dpd. One subcloned cell line obtained by this procedure, and which gave high antibody affinity for N-Dpd, is designated herein as Mab-Dpd-II-7B6-1F4-1H11(see Example 5).

The antibody reagent is prepared from the hybridoma cell line and stored by the same general procedures described above for N-Pyd Mabs.

The relative specificity of the antibody reagent for N-Dpd, N-Pyd, and other urinary pyridinium crosslinks can be determined by the approach described above (section B.1), but using a solid-phase support having attached N-Dpd.

In accordance with the procedure outlined in Example 10, the levels of binding of N-Dpd, N-Pyd, Dpd-peptides (MW>1,000), and an amino acid mixture (150 μM each of the common 20 amino acids), to monoclonal antibodies from cell line Mab-Dpd-II-7B6-1F4-1H11 were examined. The apparent Dpd concentration of each sample was determined using standard curves established using purified N-Dpd. The percent reactivity of each sample was calculated as a ratio of apparent N-Dpd concentration (measured using the N-Dpd standard curve above) to total Dpd-crosslink concentration in the sample determined by HPLC for total H-Dpd (times 100), or to total Pyd-crosslink concentration as determined by HPLC for total H-Pyd (times 100) in the case of the N-Pyd sample. The results are shown in Table 2, where reactivity with N-Dpd has been defined as 100%.

TABLE 2

| Cross-Reactivity of N-Dpd Monoclonal Antibody | |
| --- | --- |
| N-Dpd | 100% |
| N-Pyd | <1% |
| Dpd-Peptide (>1000) | 13% |
| Amino Acid Mixture (150 μM) | <1% |

As seen, the monoclonal antibody reagent is highly selective for N-Dpd relative to N-Pyd, showing a ratio of reactivity toward native free deoxypyridinoline and native free pyridinoline that is greater than about 100:1. The reagent is also selective for N-Dpd over the pyridinium-peptide forms tested (quantitated for Dpd content), showing a ratio of reactivity toward deoxypyridinoline peptides larger than 1,000 daltons in molecular weight, that is greater than about 3:1, and preferably, greater than about 5:1. In addition, the reagent shows minimal cross reactivity (<1%) with the amino acid mixture tested.

More generally, the Mab reagent which is specific for Dpd has a reactivity toward native pyridinoline (N-Dpd) and Dpd-peptides (MW>1000), of greater than about 5:1, preferably greater than 10:1, more preferably greater than 25:1, and in the present case, greater than 100:1, as measured by the above assay.

B.3 Monoclonal Antibodies Which Bind N-Pyd and N-Dpd With Comparable Affinities.

For producing a monoclonal antibody reagent which binds N-Pyd and N-Dpd with comparable affinity, the procedures described above for obtaining N-Pyd Mabs and N-Dpd Mabs can be used. The immunogen may be Pyd-KLH or Dpd-KLH, and immunoreactivity screening is done with separate assays for N-Pyd and N-Dpd. One subcloned cell line obtained by the procedure above, using H-Dpd-KLH as immunogen, and which gave high antibody affinity for both N-Dpd and N-Pyd, is designated herein as Mab Pyd/Dpd-V-6H2-2H4-1E4 (see Example 6).

The antibody reagent is prepared from the hybridoma cell line and stored by the same general procedures described above for the N-Pyd Mabs.

The relative specificity of the antibody reagent for N-Dpd, N-Pyd, and other urinary pyridinium crosslinks can be determined by the procedure described above (sections B.1 and B.2). In the present case, for antibodies produced using the Pyd/Dpd-V-6H2-2H4-1E4 cell line, the percent reactivity of each sample was calculated as a ratio of apparent N-Dpd concentration (measured using the N-Dpd standard curve above) to total Dpd crosslink concentration in the sample determined by HPLC for total H-Dpd (times 100), or to total Pyd crosslink concentration determined by HPLC for total H-Pyd in the case of the N-Pyd sample. The results are shown in Table 3, where reactivity with N-Dpd has been defined as 100%.

TABLE 3

| Cross-Reactivity of Pyd/Dpd Monoclonal Antibody | |
| --- | --- |
| N-Dpd | 100% |
| N-Pyd | 102% |
| Dpd-Peptide (>1000) | 1% |
| Pyd-Peptide (>1000) | 11% |
| Amino Acid Mixture (150 μM) | 5% |

As seen, the monoclonal antibody reagent recognizes N-Dpd and N-Pyd with comparable affinities, with a cross-reactivity ratio close to 1:1. The reagent is also selective for N-Dpd over the pyridinium-peptide forms tested (both Pyd and Dpd peptides), showing a ratio of reactivity toward pyridinium peptides larger than 1,000 daltons in molecular weight, of greater than about 3:1, and in the present case, greater than 9:1. In addition, the reagent shows minimal cross reactivity (5%) with the amino acid mixture tested.

More generally, the Pyd/Dpd-specific Mab reagent has a reactivity toward native free pyridinoline (N-Pyd) and native free deoxypyridinoline (N-Dpd) of between about 2:1 and 1:2.

C. Polyclonal Antibodies

Polyclonal antibody preparation is by conventional techniques, including injection of the immunogen into suitable mammalian subjects, such as rabbits or mice, according to immunological protocols generally known in the art, e.g., Harlow, pp. 93–115. Typically, rabbits are injected subcutaneously with the immunogen in an adjuvant, and booster immunizations are given by subcutaneous or intramuscular injection every 2–3 weeks; mice may be injected intraperitoneally according to a similar schedule. Blood is collected at intervals, e.g. 1–2 weeks after each immunization injection. Antisera may be titrated to determine antibody formation with respect to N-Pyd or N-Dpd, according to standard immuno-precipitation methods (Harlow, pp. 423–470). Details of one method for producing polyclonal antibodies in rabbits are given in Example 11.

The binding affinity constant for polyclonal antisera can be determined by known methods (e.g., by Scatchard analysis using an immunoprecipitation or ELISA assay; see Campbell, Segel), and represents an average binding affinity constant value for the antibodies in the antisera which are specific against the selected pyridinium species. Polyclonal antibodies obtained from rabbit VI-8 have a binding constant for N-Pyd of about $1 \times 10^8$, as determined by Scatchard analysis.

The relative binding specificity of the antibody reagent for the selected pyridinium species and for other pyridinium crosslinks can be determined by a competitive binding assay such as described above and detailed in Example 14. Table 4 shows the relative binding specificities of anti-Pyd antiserum obtained from rabbit VI-8, where reactivity with N-Pyd has been defined as 100%.

TABLE 4

| Cross Reactivity of N-Pyd Polyclonal Antibody | |
| --- | --- |
| N-Pyd | 100% |
| N-Dpd | <10% |
| Pyd-Peptide (MW > 1000) | <5% |
| Amino Acid Mixture | ~12% |

As seen, the antibody reagent is specific for N-Pyd, showing less than 10% cross-reactivity with NDpd, less than 5% cross-reactivity with Pyd-peptides (MW>1000), and moderate (~12%) cross-reactivity with the amino acid mixture. In accordance with one aspect of the invention, the polyclonal antibody reagent has a reactivity toward a selected native free pyridinium species (N-Pyd, N-Pyd, or both) and urinary pyridinium peptides larger than 1,000 daltons in molecular weight, of greater than 3:1, and preferably greater than about 5:1, as measured by the above antigen-competition assay.

III. Immunoassay Kit

In another aspect, the invention includes a diagnostic kit for use in assaying bone collagen degradation levels in a human subject. The kit includes an antibody reagent of the type described in the section above, which preferably has a binding constant for native free deoxypyridinoline of greater than about $5 \times 10^7$/molar, and more preferably, greater than $8 \times 10^8$/molar. The kit may also include detection means for detecting the amount of immunocomplex formed by reaction of the antibody reagent with selected pyridinium crosslinks, where the detection means is effective to measure the level of the selected crosslinks in a blood fluid sample.

Figure 1A:
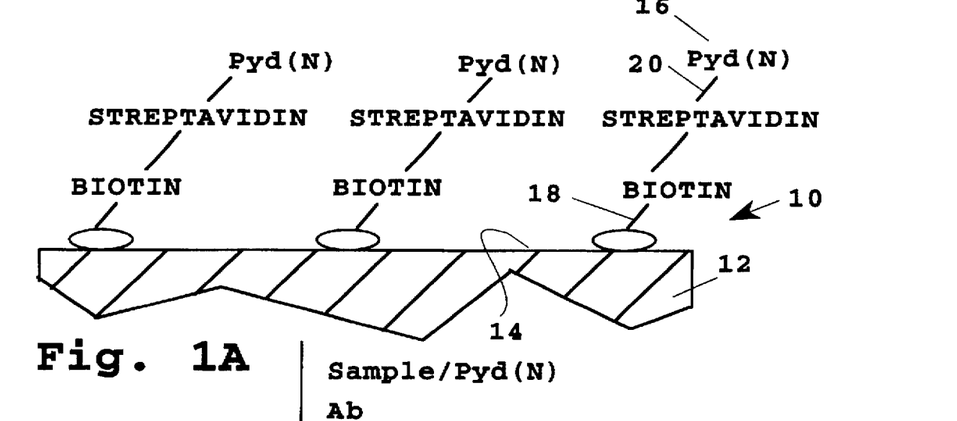
FIGS. 1A–1C illustrate steps in practicing one embodiment of the invention.
Figure 1B:
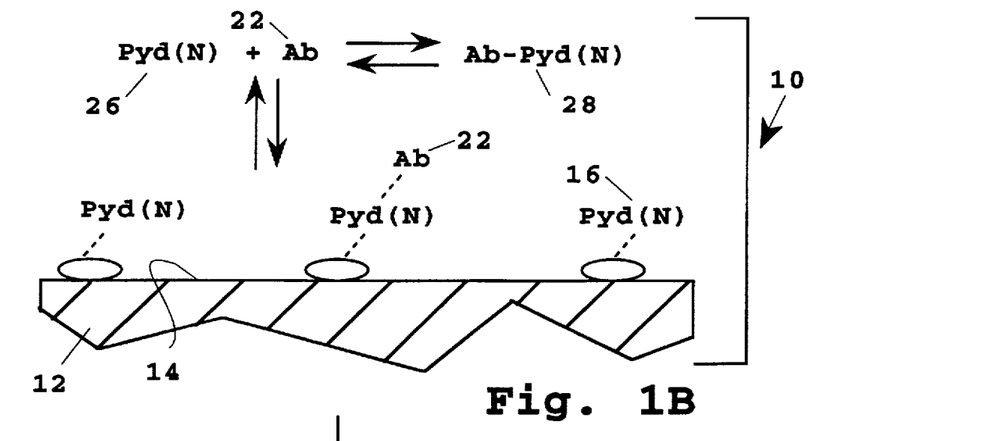
Figure 1C:
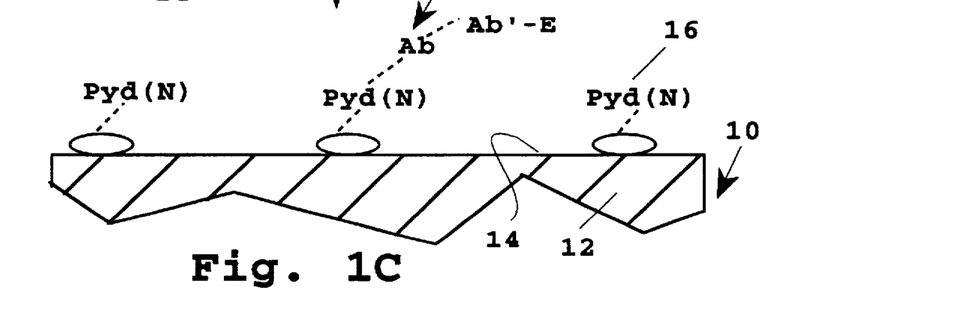

For the purpose of illustration, a specific embodiment of such a kit, for measuring N-Pyd in a sample, is shown at 10 in FIGS. 1A–1C. A solid-phase support 12 in the kit has a surface to which the binding agent can be adsorbed or chemically attached. A variety of glass and polymer resin supports having chemically derivatizable groups, or surfaces effective in protein adsorption are available. In one preferred embodiment, the kit provides 96 assay wells in a microtitre plate, where the well surfaces form the solid-phase support surfaces in the kit.

The binding agent in kit 10 is N-Pyd, indicated by Pyd(N) molecules in the figures, such as at 16. The binding agent is attached to the solid phase, in this case, each of the wells in a 96-well microtitre plate, by first adsorbing an porcine serum albumin-biotin complex, such as complex 18 in FIG. 1A, to the well surfaces, then attaching an N-Pyd-streptavidin complex, such as complex 20, to the adsorbed biotin.

The antibody reagent in the kit is indicated at 22 in FIGS. 1B and 1C, and includes the polyclonal or monoclonal reagent described in the section above. As shown in FIG. 1B, pyridinium crosslinks in a sample, such as the N-Pyd crosslink indicated at 26, competes with surface-bound N-Pyd for binding to the antibody reagent. The immunocomplex formed by reaction of the antibody reagent with sample crosslinks is indicated at 28 in this figure.

The detection reagent (detection means) in the kit is a reporter-labeled second antibody, indicated at 24 in FIG. 1C, which is effective to bind to antibody reagent which is itself bound to N-Pyd attached to the solid support. Reporter-labeled antibodies, such as enzyme-labeled antibodies, are commercially available or readily constructed (Harlow, pp. 319–358) for a variety of reporter moieties. One preferred enzyme in an enzyme-labeled antibody is alkaline phosphatase, which can react with a p-nitrophenylphosphate substrate to produce a colored product having a strong absorption peak at 405 nm.

The reporter-labeled second antibody is typically an anti-IgG antibody, such as an anti-rabbit IgG antibody, where the polyclonal antibody reagent in the kit is obtained from immunized rabbits, or an anti-mouse IgG antibody, where the antibody reagent is a mouse monoclonal antibody. Here, the antibody reagent (which is immunoreactive with N-Pyd as above) is "reporter-labelable", since the antibody reagent can become labeled by reaction with the reporter-labeled second antibody. Other instances of a reporter-labelable antibody reagent include a biotin- or streptavidin-labeled antibody which can be reacted with a reporter-labeled streptavidin or biotin-labeled partner for detection purposes.

In an alternative embodiment, the detection reagent can be the anti-Pyd antibody reagent itself, labeled with a reporter, such as an enzyme.

The detection means in the kit may also include necessary substrates or the like needed for detection of the reporter in the reporter-labeled antibody.

In an alternative kit embodiment, the binding agent attached to the support is an anti-Pyd antibody reagent such as described in Section II. The antibody may be attached to the solid support by a variety of known methods, including chemical derivatization or high-affinity binding of the antibody by support-bound protein A or anti-IgG antibody, according to standard methods. The kit may additionally include a pyridinoline reagent which is effective to compete with native free pyridinoline in a sample for binding to the antibody reagent on the support. For detection purposes, the pyridinoline reagent may include a reporter-label attached covalently to pyridinoline (i.e., the reagent can be a reporter-labeled pyridinoline). Preparation and use of an exemplary kit having this format are illustrated in Examples 7–9.

Alternatively, the pyridinoline reagent may be reporter-labelable, in that the pyridinoline reagent can include Pyd conjugated to an agent such as biotin or streptavidin, for example, for recognition by a corresponding reporter-labeled streptavidin or biotin molecule.

In another general embodiment, the kit is designed for a homogenous assay in which sample pyridinoline can be detected directly in solution.

It can be appreciated that the kit of the invention can be adapted to a number of other assay formats, including formats based on radiotracers, coupled enzymes, fluorescence, chemiluminescence, or an EMIT configuration (Gosling), for example. An exemplary EMIT assay in accordance with the invention is described in co-owned PCT Publication No. 94/03814 published Feb. 17, 1994.

Thus, in another preferred embodiment, the detection means in the kit includes a radioactive reporter group effective to produce a radioactive signal in proportion to the amount of immunocomplex formed by reaction of the antibody reagent with native free Pyd.

While the kit is illustrated above for assay of N-Pyd, it can be appreciated that a similar format can be used where the kit is for measurement of N-Dpd, using an N-Dpd specific antibody reagent, or for measurement of the sum of N-Pyd and N-Dpd, using an antibody reagent which binds N-Pyd and N-Dpd with comparable affinities.

Figure 2:
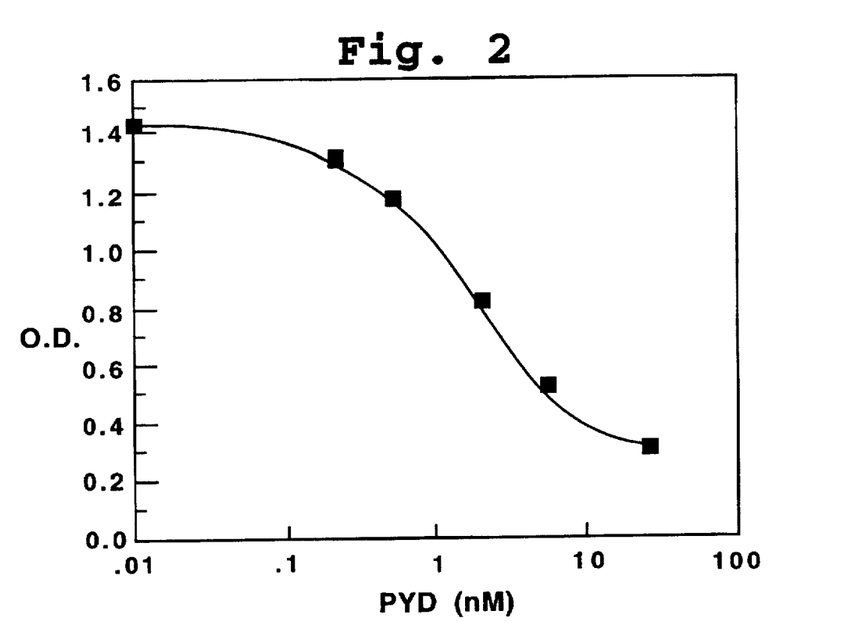
FIG. 2 is a titration curve for an antibody suitable for detecting pyridinoline (N-Pyd) in a blood fluid sample.

For detecting N-Pyd, the kit has a limit of detection for N-Pyd 1 nM or less, preferably 0.5 nM, and more preferably 0.2 nM. FIG. 2 shows an N-Pyd titration curve carried out with the immunoassay format described in Example 13, using polyclonal antiserum obtained from rabbit VI-8 characterized in Table 4. As may be seen from the figure, the kit affords a sensitivity of about 0.2 nM, while also providing reliable measurements of N-Pyd extending beyond 10 nM.

Figure 3:
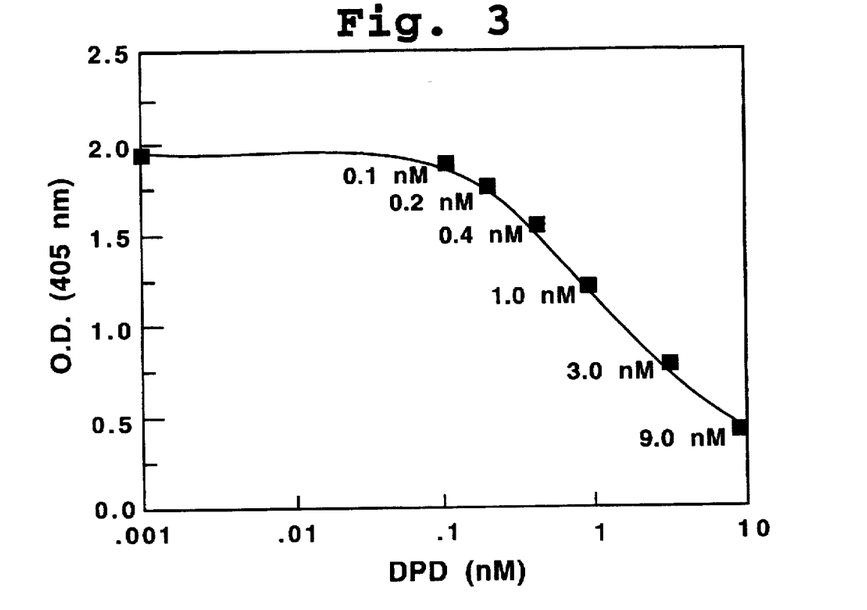
FIG. 3 is a titration curve for an antibody suitable for detecting deoxypyridinoline (N-Dpd) in a blood fluid sample.

For detecting N-Dpd, the kit preferably has a limit of detection for N-Dpd of 0.1 nM or less, preferably 0.05 nM, and more preferably 0.02 nM. FIG. 3 shows an N-Dpd titration curve carried out with the immunoassay format described in Example 9, using monoclonal antibodies obtained from the hybridoma cell line Mab-Dpd-II-7B6-1F4-1H11 noted above. As can be seen from the figure, the kit affords a limit of detection of about 0.02–0.05 nM, while also providing reliable measurements of N-Dpd extending up to about 10 nM.

It will be appreciated that the limit of detection in the kit can be selected such that only pyridinium crosslinks levels in a range considered to be above normal are detected, while those falling within generally normal levels are not detected in the assay.

IV. Immunoassay Method

The present invention provides a method of assaying bone collagen breakdown levels in a human subject, as outlined in the section above entitled "Summary of the Invention."

The blood fluid sample is preferably pretreated to remove potentially interfering substances, prior to assay of the sample. Such pretreatment may be accomplished by trichloroacetic acid precipitation, wherein the sample is mixed 10:1 with 50% trichloroacetic acid, and then centrifuged to remove the precipitate. Alternatively, the sample may be passed through a protein A column or contacted with *Staphylococcus aureus* cells (e.g., PANSORBIN cells, available from Calbiochem, San Diego, Calif.) to remove immunoglobulins and the like. In a preferred pretreatment step, the sample is filtered to remove sample components having a molecular weight of greater than about 30 kDa. Such filtration may be accomplished by centrifugation using a Centricon-30 filtration device (Amicon, Mass.).

As indicated in Section III above, the reaction of sample with the antibody reagent may be carried out in a solid-phase format, using a variety of configurations, or in a homogeneous assay format.

For illustrative purposes, the immunoassay method will be described with particular reference to an assay format for assaying native free deoxypyridinoline in serum, in accordance with Example 9, wherein the solid support has surface-attached anti-Dpd antibodies, and exogenous enymze-labeled deoxypyridinoline capable of competing with native free deoxypyridinoline from the sample for binding to the support-bound anti-Dpd antibody. It will be appreciated how the method can be adapted to other solid-phase or homogeneous assay formats.

In an exemplary embodiment of the method, a known volume, e.g., 100 µl, of the filtered or precipitated serum sample is added to an anti-Dpd-antibody-coated solid support, e.g., the wells in a microtitre plate prepared as in Example 8. Sample addition is followed by addition of a known volume, typically 50–200 µl, of reporter-labeled Dpd at a known dilution. In Example 9, the reporter-labeled Dpd is an alkaline phosphatase-Dpd conjugate, i.e., enzyme-labeled Dpd. The mixture on the solid support surface is then incubated, preferably under conditions effective to achieve equilibrium for binding of the anti-Dpd antibody with sample Dpd and enzyme-labeled Dpd. In the method detailed in Example 9, the incubation is overnight at 4° C.

After incubation, the support is again washed to remove non-specifically bound material, and the level of enzyme bound to the support is determined by addition of enzyme substrate, with spectrophotometric determination of converted substrate. Details are given in Example 9.

In a typical assay, N-Dpd standards containing increasing concentrations of N-Dpd are added in duplicate to some of the wells, for purposes of generating an N-Dpd concentration standard curve. Up to 40 samples are then added in duplicate to remaining wells, and the wells are then assay as above. The standard curve is used for determining pyridinium crosslink values for the samples in terms of N-Dpd concentrations.

V. Applications

The immunoassay method, antibody reagent, and kit of the invention, described above, are useful in assaying the level of collagen breakdown activity in a human subject.

In general, the invention is useful in detecting increased blood levels of Pyd and Dpd associated with bone collagen breakdown conditions in general. Such conditions may include osteoporosis, Paget's disease, hypothyroidism, osteoarthritis, and rheumatoid arthritis, for example. Other conditions involving increased native free pyridinium crosslinks levels include various forms of metastatic cancer which become established in bone tissue or which otherwise alter bone metabolism. The method is also useful in monitoring the course of a bone metabolism disorder, such as noted above, and in monitoring therapy. In this embodiment, free crosslink measurements are obtained periodically to assess the course of collagen degradation over time, with or without therapeutic treatment to counter the disorder.

Figure 4:
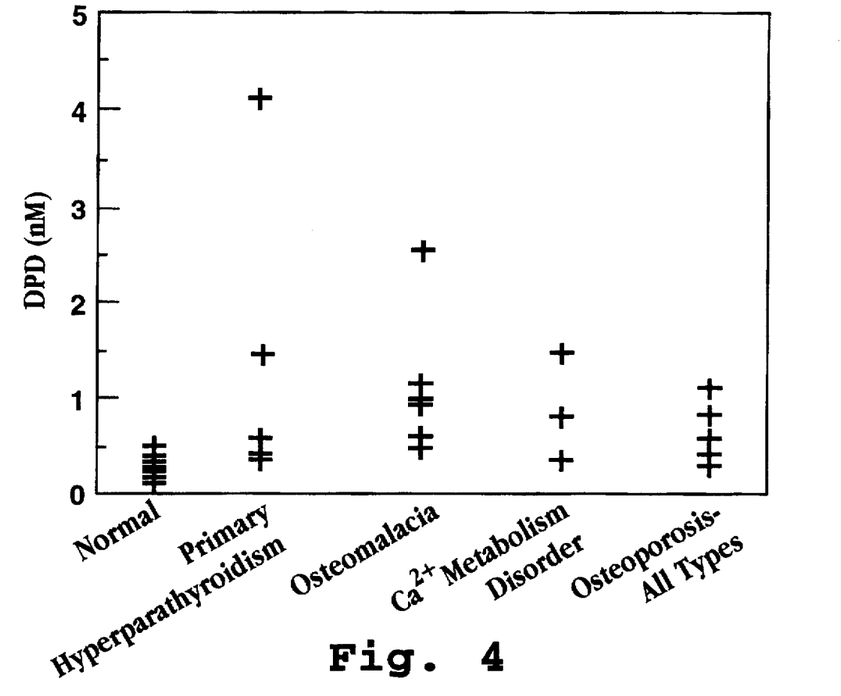
FIG. 4 shows concentrations of N-Dpd measured in serum samples from normal (control) subjects (column 1), patients with primary hyperparathyroidism (column 2), osteomalacia (column 3), calcium metabolism disorder (column 4), and osteoporosis (column 5)

Use of the method of the invention for detecting elevated levels of serum Dpd is illustrated in FIG. 4, which shows N-Dpd levels measured in serum samples from healthy (control) patients (column 1), and in serum samples from patients with primary hyperparathyroidism (column 2), osteomalacia (column 3), calcium metabolism disorder (column 4), and osteoporosis (column 5). The study was carried out using the assay protocol described in Example 9, with antibodies from hybridoma cell line Mab-Dpd-II-7B6-1F4-1H11 (see Table 2 above).

As can be seen from the Figure, N-Dpd levels in the control group were between about 0.2 and 0.5 nM, with an average level (± standard deviation) of 0.33±0.07 nM. The primary hyperparathyroidism group showed levels between about 0.4 and 1.4 nM, with one patient showing a level of about 4.2 nM (mean=1.4 nM). The osteomalacia group showed levels between about 0.5 and 2.6 nM (mean 1.2 nM); the calcium metabolism disorder group showed levels between about 0.4 and 1.4 nM (mean 0.9 nM); and the osteoporosis group showed levels between about 0.3 and 1.1 nM (mean 0.6 nM).

The FIG. 4 data from the diseased groups as a whole are consistent with increased collagen breakdown in these patients. The results show that serum N-Dpd levels above about 0.8 nM, and more preferably, above about 0.5 nM, are a useful indicator of increased collagen breakdown in such patients.

Figure 5:
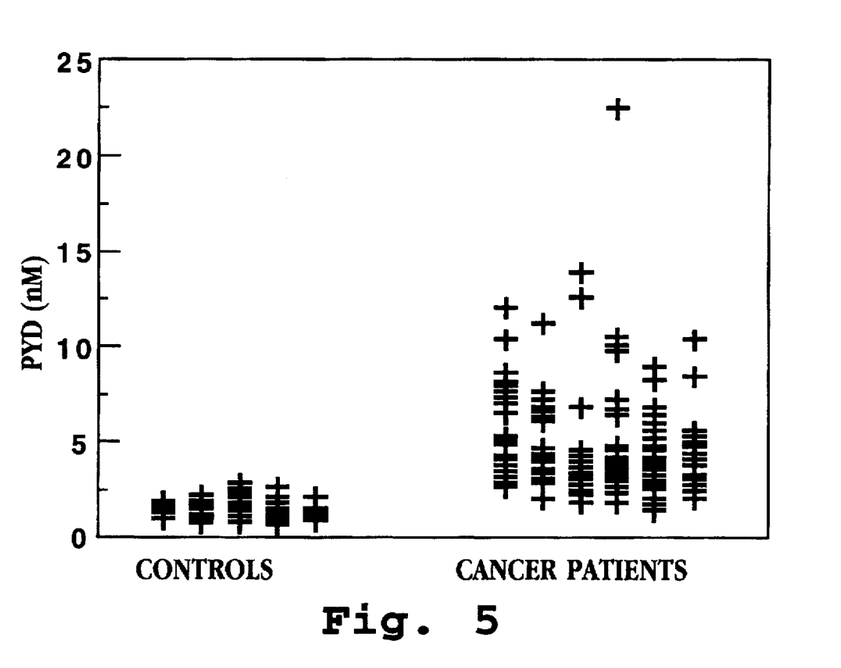
FIG. 5 shows concentrations of serum Pyd measured in accordance with the present invention in healthy control patients and in cancer patients.

FIG. 5 compares N-Pyd levels measured in serum samples from a group of healthy patients (group 1) with levels measured in samples from a group of cancer patients with established or suspected bone metastases. The study was carried out using the assay protocol described in Example 13, with antibodies from rabbit VI-8 characterized above in Table 4. As can be seen from the Figure, N-Pyd levels in the control group were between about 1 and 3 nM, with an average level (± standard deviation) of 1.7±0.4 nM. The cancer group, on the other hand, showed levels between about 2 and 13 nM, with one patient showing a level of about 23 nM, consistent with increased collagen breakdown in these patients. The results show that serum N-Pyd levels above about 5 nM, more preferably above about 3 nM, is a useful indicator of increased collagen breakdown in such patients.

From the foregoing, it can be appreciated how the objects of the invention are met. By employing a blood fluid sample, the assay method allows measurement of native free pyridinium crosslink levels to be integrated with other clinical tests with blood samples. The approach also avoids the correction for variation in sample volume typically needed where the sample is a urine sample (e.g., determination of urinary creatinine). The assay utilizes an antibody reagent, and can thus be adapted to a number of convenient and rapid assay formats, such as described above. The invention can be used both for detecting increased collagen degradation in a patient, and also for monitoring the course of therapy of a variety of collagen-pathology states.

The following examples illustrate methods of producing antibody reagents and assay methods in accordance with the invention. The examples are intended to illustrate, but in no way limit, the scope of the invention.

EXAMPLES

Materials and Methods

Female autoimmune MRL/MpJ-lpr mice were purchased from the Jackson Laboratory, Bar Harbor, Me.

Mouse non-secreting P3X63Ag8.653 myeloma cells, and mouse monocyte-macrophage cell lines P388D1(IL-1) and J774A.1 were purchased from American Type Culture Collection (ATCC), Rockville, Md.

Adjuvant Ribi and Ribi(CWS) were purchased from RIBI Immunochem Research, Inc., Hamilton, Mont. 50% PEG 1500 (polyethylene glycol 1500, 50% (w:v) in water) was purchased from Boehringer Mannheim, Indianapolis, Ind. HAT and HT were purchased from Sigma Chemical Company, St. Louis, Mo.

Dulbecco's Modified Eagle Medium (DMEM), NCTC-109, and gentamicin were purchased from Gibco, Grand Island, N.Y. Fetal clone bovine serum was from Hyclone Laboratories, Inc., Logan, Utah. Oxaloacetic acid and insulin were from Sigma Chemical Company. S-DMEM was formulated as follows, where the percentages indicate final volume percentages in the final medium: DMEM (80%), NCTC-109 (10%), fetal clone bovine serum (10%), oxaloacetic acid (1 mM), L-glutamine (2 mM), gentamicin (50 µg/ml) and insulin (10 µg/ml).

For preparation of conditioned media, mouse monocyte cell lines P388D1 (IL-1), or interchangeably, cell line J774A.1, were grown in S-DMEM medium, with a 1:4 split twice a week. Every 3 days, tissue culture supernatants were filtered through a 0.2 micron filter and then supplemented with 4 mM L-glutamine. The resultant concentrated conditioned media were used as 20% supplement for S-DMEM to raise hybridoma cells.

Unless stated otherwise, PBS is defined as a buffer containing 0.01M phosphate and 150 mM NaCl, pH 7.

Example 1

HPLC Measurement of Crosslinks

HPLC analysis for Pyd and Dpd was done essentially as described in Black (1988). Briefly, urine samples were adjusted with butanol and glacial acetic acid to 4:1:1 (v:v:v) mixture and applied onto CF1 cellulose (Whatman) cartridge, followed by a wash with 4:1:1 (butanol:acetic acid:water) solution. Only free crosslinks were retained. The free crosslinks were eluted from CF1 cellulose with water. Eluted material was analyzed on a C18 reverse phase column (Rainin, C18-80-200-C3) using a water-acetonitrile (3–17% in 10 minutes) gradient delivered at 1 ml/minute and monitoring fluorescence at 295 nm of excitation, 395 nm of emission. Mobile phase contained 0.1% HFBA.

Total urinary crosslinks were measured by hydrolyzing a urine sample in HCl (6N) at 110° C. for 16 hours, followed by the CF1 pretreatment and HPLC analysis as above. HPLC separation yielded hydrolysed Pyd and Dpd fractions, from which T-Pyd and T-Dpd were quantitated.

Example 2

Purification of Crosslinks

Human urine was filtered through 3000 dalton molecular cut off filter (Filton Co.) applying 40 psi of back pressure. The filtrate was then lyophilized and reconstituted to 1/20 of the original volume with 0.2M acetic acid.

Concentrated urine was then applied onto Sephadex G-10 2.6×95 cm column equilibrated with 0.2M acetic acid.

Elution from the column material was analyzed for free Pyd and Dpd as described above. The free crosslink containing fractions were pooled together, adjusted to pH 2.0 and applied onto 1×18 cm cation exchange column (Lacarte Co., UK) and equilibrated with 0.1M sodium citrate pH 4.2.

Glyco-Pyd, Pyd and Dpd were coeluted thereafter from the ion exchange column with 0.1M sodium citrate pH 4.2. Collected fractions were analyzed for the presence of crosslinks by HPLC analysis as above. Fractions containing specific crosslinks (glyco-Pyd, Pyd and Dpd) were pooled together and applied onto 2.5×10 cm reverse phase C18 column (Waters) which was subsequently developed with 2–20% gradient of acetonitrile containing 0.1% HFBA. Separated fractions (glyco-Pyd, Pyd and Dpd) were collected and concentrated by lyophilization. Dry residue was reconstituted in 0.2M acetic acid and stored at 4° C. Purity of the final material was measured by gravimetric and elementary analysis.

Urinary crosslink-peptides were prepared by exhaustive dialysis of human urine using 1000 D molecular weight cut off dialysis membranes (Spectra-Por). The T-Pyd and T-Dpd crosslink content of the peptide fractions was determined by hydrolyzing peptide samples with 6N HCl at 110° C. for 16 hours followed by HPLC analysis for Pyd and Dpd.

Preparative amounts of H-Pyd and H-Dpd were obtained from hydrolyzed powdered bovine or sheep bone as described by Black et al. (1988).

Example 3

Preparation of Immunogens

The following procedures illustrates how immunogens can be prepared for obtaining monoclonal or polyclonal antibodies against native free pyridinoline, native free deoxypyridinoline, or both. The procedures in A and B below are described with respect to Pyd-immunogens; Dpd-immunogens are prepared the same way, but using Dpd instead of Pyd.

A. Pyd-BSA Immunogen

To a 3.1 ml solution consisting of 9 mg of bovine serum albumin (BSA) and 3.8 mg of Pyd in 0.1M MES pH 5.0 was added an 0.88 ml aqueous solution containing 88 mg of EDC. The mixture reacted for four hours at room temperature then was exhaustively dialyzed versus phosphate buffered saline pH 7.0 (PBS). UV and fluorescence measurements indicated 5.8 moles of pyridinoline substituted per mole of albumin.

B. Pyd-KLH Immunogen

To a solution of dried H-Pyd (6 mg) in water adjusted to pH 5±0.5 (200 µl) was added 2 ml of a 10 mg/ml solution of keyhole limpet hemocyanin (KLH) in PBS. To the mixture was added 30 mg solid 1-(3-dimethylaminopropyl)-3-ethylcarbodiimide (EDC, Pierce), and ten minutes later, another 30 mg of EDC, and the reaction was allowed to proceed for 4 h at room temperature. The reaction mixture was then exhaustively dialyzed versus PBS, after which the Pyd-KLH immunogen was collected and stored.

Example 4

Preparation of Anti-Pyd Monoclonal Antibodies

A. Immunization Protocol

Female 5-week-old autoimmune MRL/MpJ-lpr mice were immunized using the protocol below:

TABLE 5

Immunization Protocol for Pyd Mice

| Immunization | Days from Fusion | Immunogen Injected (µg) | [1]Adjuvant | Inject. Mode |
|---|---|---|---|---|
| 1 | 60 | 100 | Ribi | ip[2] |
| 2 | 46 | 100 | Ribi | ip |
| 3 | 32 | 100 | Ribi | ip |
| 4 | 18 | 100 | Ribi | ip |
| 5 | 4 | 200 | — | iv[3] |

[1]Adjuvant and antigen were suspended in Hank's balanced salt solution
[2]Intraperitoneal
[3]Intravenous On the day of fusion, the immunized mouse was sacrificed by $CO_2$ gas, and the spleen was excised from the mouse and placed in a culture dish containing 5 ml of serum-free DMEM medium preheated to 37° C. Following removal of adipose tissue attached to the spleen, the spleen was washed with 5 ml of serum-free DMEM medium. The spleen was then cut into small pieces which were placed in a cell homogenizer containing 7 ml of serum-free DMEM medium, and the cells were homogenized to form a cell suspension.

B. Fusion Protocol

The following steps were performed at room temperature.

The spleen cell suspension (~2×10⁸ cells in serum-free DMEM medium) and log-phase P3X63Ag8.653 myeloma cells (~7×10₇ cells in serum-free DMEM medium) were centrifuged independently at 400×g for 10 min. The resultant cell pellets were suspended together in serum-free DMEM medium (10 ml) in a 50 mL centrifuge tube and then centrifuged at 400×g for 10 min. The supernatant was removed completely, and the centrifuge tube was tapped to loosen the cell pellet.

For cell fusion, a solution of 50% PEG 1500 (4 ml) was added dropwise to the tube with gentle mixing by pipette over a 90 second period. Next, serum-free DMEM (4 ml) was added dropwise over 1 min. S-DMEM (40 ml) was then added over 2 min with gentle mixing, after which the mixture was mixed by pipette for an additional 2.5 min. The resultant mixture was centrifuged at 400×g for 10 min. After thorough removal of the supernatant, the cells were suspended in 320 ml of HAT in 20% P388D1-conditioned S-DMEM medium. The cell suspension was plated in 16 96-well tissue culture plates, 200 µl/well, and the plates were then incubated at 37° C. in an atmosphere containing 7% $CO_2$. The cell mixtures were fed at day 3 and day 7 by removing 100 µl/well of old medium and adding 150 µl/well of either HAT medium (day 3) or HT medium (day 7). The wells were ready to screen 7 to 10 days after fusion.

C. Screening Hybridomas for Production of Anti-N-Pyd Monoclonal Antibodies

Successful fusion products were screened for immunoreactivity using the N-Pyd immunoassay format described in Examples 12 and 13. Cell lines which showed high affinity binding to N-Pyd were subcloned by limiting dilution and further screened for production of antibodies with high binding affinity for N-Pyd. One of the subcloned cell lines which gave high antibody affinity for N-Pyd is designated herein as Mab Pyd-XXV-3G6-3B11-1A10. The specificity of antibodies produced by this cell line is shown in Table 1 above.

Example 5

Preparation of Anti-Dpd Monoclonal Antibodies

Anti-Dpd monoclonal antibodies were prepared by the procedure described in Example 4, using Dpd-KLH immunogen prepared as in Example 3. The mouse immunization procedure was the same as in Example 4, except that Ribi(CWS) was used as adjuvant instead of Ribi, and 75 µg Dpd-immunogen per mouse was used in the fourth immunization step (18 days from fusion) instead of 100 µg.

Successful fusion products were screened for immunoreactivity using the N-Dpd immunoassay format described in Example 9. Cell lines which showed high affinity binding to N-Dpd were subcloned by limiting dilution and further screened for production of antibodies with high binding affinity for N-Dpd. One of the subcloned cell lines which gave high antibody affinity for N-Dpd is designated herein as Mab Dpd-II-7B6-1F4-1H11. The specificity of antibodies produced by this cell line is shown in Table 2 above.

Example 6

Preparation of Monoclonal Antibodies Specific for Both N-Pyd and N-Dpd

Monoclonal antibodies specific for both N-Pyd and N-Dpd were prepared by the procedure in Example 5, using H-Dpd-KLH (Example 3) as immunogen. Successful fusion products were screened for immunoreactivity using the N-Dpd immunoassay format described in Example 9. Cell lines which showed high affinity binding to N-Dpd were subcloned by limiting dilution and further screened for production of antibodies with high binding affinity for both N-Pyd and N-Dpd. One of the subcloned cell lines which gave high antibody affinity for both N-Pyd and N-Dpd is designated herein as Mab Pyd/Dpd-V-6H2-2H4-1E4. The specificity of antibodies produced by this cell line is shown in Table 3 above.

Example 7

Alkaline Phosphatase-H-Dpd conjugate

Alkaline phosphatase-H-Dpd conjugate was prepared using bis(sulfosuccinimidyl)suberate (BSSS) as a coupling agent. In brief, 425 µL of a 7.1 mg/mL solution of alkaline phosphatase (AP, 3 mg, 140,000 MW, $\epsilon=0.963$ mg/mL$^{-1}$ cm$^{-1}$) (Biozyme Laboratories, San Diego, Calif.) dialyzed the previous night at 4° C. in PBS was mixed with 24 µL of an 11 mg/mL solution (0.27 mg) of H-Dpd ($\epsilon=4933$ M$^{-1}$ cm$^{-1}$) in 0.1M phosphate buffer, pH 7.5, and the volume of the resultant mixture was adjusted to 500 µL with PBS.

To the mixture was then added 0.61 mg of BSSS (Pierce, Rockford, Ill.) dissolved in 50 µL DMSO (dimethylsulfoxide). The reaction vessel was covered to exclude light, and the coupling reaction was allowed to proceed at room temperature for 2 hours. The reaction was then quenched by adding 500 µl of 10 mM glycine (in 0.1M phosphate buffer pH 7.5) and allowing the mixture to incubate for another 2 hours at room temperature, covered from light. The quenched reaction mixture was then dialyzed against four changes of PBS (2 L each, at four hour intervals) at 4° C. in darkness.

The stoichiometry of Dpd to AP in the dialyzate was determined spectrophotometrically by measuring the absorbances at 326 nm and 280 nm. The ratio of Dpd to AP was typically from 1:1 to 2:1. The enzymatic activity of the AP-H-Dpd conjugate was determined as a percent of the activity of native AP in a standard AP assay.

Example 8

Preparation of Anti-Dpd-Antibody Coated Plates 96-well ELISA plates were coated as follows. 200 µl of a solution containing 3 µg/ml rabbit anti-mouse IgG in PBS containing 0.05% NaN₃ were added to each well, and the plates were incubated 18–24 hours at room temperature. After the incubation, the plates were washed 3× with 300 µl per well of wash buffer (PBS containing 0.3% Tween 20). After aspiration of the wells in the final wash, 150 µl of capture solution containing 100 mM phosphate, 150 mM NaCl, 0.05% Tween-20, 0.05% NaN₃, 0.1% bovine serum albumin, and 10 ng/ml of mouse anti-Dpd monoclonal antibody (13D4), pH 7, was added to each well. The plates were incubated for 18–24 hours at room temperature. After the incubation was complete, each well was washed 3× with wash buffer as above. After final aspiration of the wells, 250 µl of a preservative solution containing 10% sucrose, 100 mM phosphate, 150 mM NaCl, and 0.05% NaN₃ (pH 7) were added to each well, and the plates were incubated for 1 hour at room temperature. The preservative solution was then removed by aspiration, and the plates were placed at 37° C., ≦10% humidity, for 18–24 hours. The coated plates were sealed in foil with a dessicant packet and stored at room temperature.

Example 9

Immunoassay for Serum Dpd

N-Dpd standard solutions and serum samples were tested in duplicate. The standard solutions typically consisted of 0, 0.05, 0.1, 0.2, 0.4, 1.0, 3.0, and 9.0 nM N-Dpd in 10 mM PBS containing 0.05% NaN₃ and 10 mg/mL bovine serum albumin.

To a 400 µl aliquot of each standard solution or serum sample was added 40 µl of 50% v:v aqueous trichloroacetic acid (TCA), and the resultant mixtures were vortexed briefly and centrifuged at 10,000 rpm for 5 minutes. The supernatant was collected (300 µl) from each centrifuge tube, and the pH was adjusted to pH 7.0±0.5 with 3N NaOH.

To each well of an anti-Dpd-antibody-coated plate from Example 8 was added 100 ul of TCA-precipitated standard or serum sample, and 50 µl of Dpd-alkaline phosphatase solution (containing ~75 ng/mL Dpd-AP conjugate, 100 mM PBS, 0.7% bovine serum albumin, 0.3% sucrose, 7 mM Tris, 0.15 mM MgCl₂, 0.05% Tween-20, and 0.05% azide). After incubation of the plates overnight at 4° C., the wells were washed with PBS containing and 0.05% NaN₃ and 0.05% Tween-20.

Dpd-alkaline phosphatase conjugate retained in each well was assayed by adding to each well 150 µL of substrate solution (p-nitrophenyl phosphate, 2 mg/mL in 1M diethanolamine, pH 10, containing 1 mM MgCl), incubating at room temperature for one hour, stopping the enzymic reaction by addition of 50 µL 3N NaOH, and reading the optical density of the well at 405 nm using a Vmax reader (Molecular Devices Corp.). The Dpd crosslink concentration for each serum sample was determined by comparison with a standard curve constructed with the N-Dpd standard solutions.

Example 10

Binding Selectivity of Antibody Reagent

N-Pyd, N-Dpd, and pyridinium-peptides (MW>1000) were isolated from urine samples as described above. Aliquots of the pyridinium-peptide fraction were hydrolysed to convert the crosslinks in the fraction to H-Pyd and H-Dpd. The concentrations of Pyd in the N-Pyd and H-Pyd preparations, of Dpd in the N-Dpd and H-Dpd preparations, and of Dpd in the pyridinium-peptide preparation, were determined by HPLC, as in Example 1. In addition, an amino acid solution containing an equimolar mixture of the 20 common amino acids, 150 µM each in PBS, was prepared.

Aliquots (50 µl) of the native crosslink preparations and the amino acid mixture were added in duplicate to anti-Dpd-antibody-coated microtitre wells (Example 8), and each well was assayed for ND-pd as in Example 9, except that 100 µL Dpd-AP conjugate solution was used rather than 50 µL. The optical density readings (405 nm) from duplicate samples were averaged, and from these values, the apparent N-Dpd concentration of each sample was determined using a standard curve established with purified N-Dpd. The percent reactivity of each sample was calculated as a ratio of apparent N-Dpd concentration (measured using the N-Dpd standard curve above) to total Dpd crosslink concentration in the sample determined by HPLC for total H-Dpd (times 100). The relative reactivity determined for purified N-Dpd was arbitrarily set at 100%, and the reactivities of the other crosslink preparations (and the amino acid mixture) were expressed as a percentage of 100. Results obtained with this assay are shown in Table 2 above.

Example 11

Preparation of Anti-Pyridinoline Antiserum

New Zealand white rabbits (a total of 59) for immunization were divided into eight groups according to immunization protocol, as indicated below in Table 6. The immunization dose was 200 µg of Pyd-BSA (Example 3A), low-hapten Pyd-BSA immunogen (prepared as in Example 3A for Pyd-BSA, but with a lower Pyd:BSA stoichiometry), or Pyd-KLH (Example 3B), in 1.0 ml PBS mixed with 1.0 ml of Ribi adjuvant (Ribi ImmunoChemical Research, Inc.). Initial immunization was by subcutaneous injections at multiple sites, and subsequent booster immunizations were given at three week intervals intramuscularly. Antiserum was collected 10 days after each immunization.

TABLE 6

| Group | # Rabbits | Rabbits Kept | Carrier |
| --- | --- | --- | --- |
| I | 4 | 1 | BSA |
| II | 10 | 0 | BSA |
| III | 10 | 2 | BSA |
| IV | 5 | 1 | BSA |
| V | 5 | 2 | BSA |
| VI | 10 | 1 | KLH |
| VII | 5 | 0 | Low Hapten BSA |
| VIII | 10 | 1 | BSA |
| Total | 59 | 8 | |

Upon collection, each antiserum was tested for Pyd binding affinity using the assay format described in Example 13. In brief, binding of anti-Pyd antibodies from the serum to Pyd immobilized on a solid support was detected using an alkaline phosphatase-labeled goat anti-rabbit IgG antibody reagent.

Immunized animals were kept if their antisera satisfied the following criteria, defined further in the following paragraph: AA <20%, Pyd-peptide <10%, titer >5000, and a 0 to 25 nM Pyd signal separation of >10% of total modulated signal.

Profiles of the most strongly reactive antisera are shown in Table 7 below, as measured using the assay format described in Example 13. The first column indicates the immunization program from which the rabbit antiserum came. The second column indicates the bleeds which were used for analysis. The column marked "titer" indicates the average dilution of each antiserum necessary to achieve an optical density reading of 1.2 to 1.6 with a Pyd-negative sample (no Pyd present) in the immunoassay. The column marked "AA" shows the average cross-reactivity of each antiserum with the amino acid mixture described in Example 7. The column marked "Pyd-pep >1000 MW" shows the average cross-reactivity of each antiserum with Pyd-peptides (>1000 MW). The last column shows the separation between signals for 0 and 25 nM Pyd samples as a fraction of the total modulated signal.

TABLE 7

| Rabbit # | Bleeds | Titer | AA | Pyd-pep. >1000 MW | Sens. 25 nM |
|---|---|---|---|---|---|
| I-3 | 21–28 | 200K[1] | 2% | 4.6% | 18% |
| III-3 | 11–18 | 20K | 16% | 8.3% | 37% |
| III-5 | 11–18 | 52K | 1% | 8.1% | 13% |
| IV-4 | 4–14 | 84K | 4% | 4.9% | 10% |
| V-3 | 4–14 | 22K | 18% | 4.0% | 15% |
| V-4 | 11–14 | 9700 | 15% | 5.2% | 29% |
| VI-8 | 2–11 | 30K | 10% | 0.6% | 61% |
| VIII-4 | 3–10 | 34K | ~0% | 3.4% | 11% |

[1]K = × 1000.

As can be seen, rabbits III-3, V-4, and VI-8 showed significant modulation of signal from 0 to 25 nM N-Pyd. The serum with highest activity (VI-8) was selected for use in the N-Pyd assays described herein.

Example 12

Preparation of Pyd-Coated Microplates

Biotin-labeled porcine ovalbumin and a streptavidin-Pyd conjugate were utilized in the microplate coating. Biotinylation of the ovalbumin was carried out by adding 10 mg of biotin-X-2,4-dinitrophenol-X-L-lysine, succinimidyl ester (Molecular Probes) in 400 microliters of dimethylformamide to a 10 ml solution of PBS containing 150 mg of ovalbumin. The mixture was allowed to react for two hours at room temperature, followed by G25 column chromatography. Spectrophotometric analysis indicated two biotins substituted per mole of ovalbumin.

Conjugation of N-Pyd to streptavidin was accomplished by coupling a thiolated streptavidin to N-Pyd via the coupling agent, SMCC. Thiolated streptavidin was prepared by reaction with N-succinimidyl-3-(2-pyridylthio)propionate (SPDP, Pierce) as follows. To a 0.75 ml solution of 5 mg of streptavidin in PBS was added 21 uL of dimethylformamide containing 260 ug of SPDP. The mixture was allowed to react for one hour at room temperature, and then was dialysed against PBS. The SPDP-labeled streptavidin was reduced by the addition of dithiothreitol to a final concentration of 10 mM. After incubation for one hour at room temperature, the thiolated streptavidin was purified on a G-25 column.

To form N-Pyd-streptavidin, a solution containing 180 ug of succinimidyl 4-(N-maleimidomethyl)cyclohexane-1-carboxylate (SMCC, Pierce) in dimethylformamide (4 ul) was added to a solution containing 0.5 mg thiolated streptavidin and 50 ug of N-Pyd in 100 µl of PBS. The mixture was allowed to react for 3 hours at room temperature and then was dialysed versus PBS. Spectrophotometric analysis of the resultant Pyd-streptavidin indicated between 1 and 6 equivalents of pyridinoline bound per equivalent of streptavidin.

Each of the wells in a 96-well ELISA plate were coated with with N-Pyd as follows. To each well was added 150 microliters of biotin-ovalbumin solution at 3.8 ug/ml in PBS, followed by an overnight incubation at 2°–8° C. The microplates were washed with PBS and blocked by adding 200 ul of ovalbumin at 1 mg/ml with an overnight incubation at room temperature. The microplates were then twice washed with PBS. The streptavidin-Pyd conjugate is immobilized via the streptavidin mediated binding to biotin. 150 ul of a solution containing streptavidin-Pyd at 100 ng/ml in PBS was added to each well of the biotin-ovalbumin coated microplate. After a one hour incubation at room temperature, the plates are twice washed with PBS, and then with 200 µL of 10% sucrose in 100 mM PBS for 2 hours. Residual liquid was removed from the microplate by drying overnight in a convection oven at 37° C.

Example 13

Immunoassay for Pyd Using Polyclonal Antibody Reagent

The following immunoassay was performed using rabbit polyclonal antibody VI-8 characterized in Tables 4 and 7 above, and the N-Pyd-coated microtiter plate described in Example 12.

N-Pyd standard solutions and blood serum samples were tested in duplicate. The standard solutions consisted of 0 nM, 0.2 nM, 0.6 nM, 2.0 nM, 6.0 nM, and 24 nM N-Pyd in assay buffer (0.05% NaN3, 0.05% Tween 20, and 0.1% BSA in 100 mM sodium phosphate containing 150 mM NaCl, pH 7). Serum samples were filtered through a Centricon-30 filter device (Amicon, Mass.) prior to assay.

Following the addition of sample or standard (25 µl/well), 125 ul/well of VI-8 antiserum diluted 20,000-fold in assay buffer was added, and the assay plate was incubated at 4° C. overnight. After the plate was washed 3 times with 300 µl/well of wash buffer, 150 µl/well of goat anti-rabbit IgG-alkaline phosphatase conjugate (1:1000 dilution in assay buffer) was added, and the plate was incubated at room temperature for 1 h. The wells were then washed 3 times with wash buffer.

To each well was added 150 uL of enzyme substrate solution (2 mg/mL of p-nitrophenylphosphate (Sigma) in 1.0M diethanolamine, pH 9.8, containing 1 mM $MgCl_2$). Following a 1 hour incubation at room temperature, 50 µl of 3.0N NaOH was added to each well to stop the enzymatic reaction. The optical density at 405 nm was then measured with a Vmax reader (Molecular Devices Corp.).

The optical density readings (405 nm) from duplicate samples were averaged, and the averaged readings from the N-Pyd standards were used to construct a standard curve of OD reading vs. N-Pyd concentration. From this curve, the free N-Pyd crosslink concentration in each serum sample was determined.

Example 14

Binding Selectively of Polyclonal Antibody Reagent

N-Pyd, N-Dpd, and pyridinium-peptides (MW>1000) were isolated from urine samples as described above. Aliquots of the pyridinium preparations were hydrolysed to convert the crosslinks in the fractions to H-Pyd and H-Dpd. The concentrations of Pyd in the N-Pyd and H-Pyd preparations, of Dpd in the N-Dpd and H-Dpd preparations, and of Pyd in the pyridinium-peptide preparation, were determined by HPLC, as in Example 1. In addition, an amino acid solution containing an equimolar mixture of the 20 common amino acids, 150 µM each in PBS, was prepared.

Aliquots (50 µl) of the native crosslink preparations and the amino acid mixture were added in duplicate to Pyd-coated microtitre wells, and each well was assayed for pyridinoline as in Example 13. The optical density readings (405 nm) from duplicate samples were averaged, and from these values, the apparent N-Pyd concentration of each sample was determined using a standard curve established with purified N-Pyd. The percent reactivity of each sample was calculated as a ratio of apparent concentration (measured using the N-Pyd standard curve above) to total Pyd crosslink concentration in the sample determined by HPLC for total H-Pyd (times 100). The relative reactivity determined for purified N-Pyd was arbitrarily set at 100%, and the reactivities of the other crosslink preparations (and the amino acid mixture) were expressed as a percentage of 100. Results are shown in Tables 4 and 7.

Although the invention has been described with respect to particular embodiments, it will be appreciated that various changes and modifications can be made without departing from the invention.

It is claimed:

1. A method of assaying bone collagen breakdown levels in a human subject, the method comprising reacting a non-hydrolyzed blood fluid sample from a human subject with an antibody which is specific for native peptide-free pyridinium crosslinks selected from the group consisting of native peptide-free pyridinoline (N-Pyd), native peptide-free deoxypyridinoline (N-Dpd), or both N-Pyd and N-Dpd, wherein said antibody is produced by immunizing an animal with hydrolyzed pyridinoline or hydrolyzed hydroxypyridinoline and said antibody has a ratio of reactivity toward said selected pyridinium crosslinks and urinary pyridinium peptides larger than 1,000 daltons in molecular weight, of greater than about 5:1, by said reacting, forming an immunocomplex between the antibody and such native peptide-free pyridinium crosslinks in the sample, measuring the amount of immunocomplex formed, and by said measuring, determining the concentration of such selected native peptide-free pyridinium crosslinks in the sample, wherein a determined concentration that is above (i) 5 nM N-Pyd, (ii) 1 nM N-Dpd, or (iii) 6 nM combined N-Pyd and N-Dpd indicates the presence of an above-normal level of collagen breakdown in the subject.

2. The method of claim 1, wherein the antibody has a binding constant for said selected crosslinks of at least $5 \times 10^7$/molar.

3. The method of claim 2, wherein said antibody is a monoclonal antibody.

4. The method of claim 3, wherein said monoclonal antibody is specific for N-Pyd.

5. The method of claim 3, wherein said monoclonal antibody is specific for N-Dpd.

6. The method of claim 3, wherein said monoclonal antibody is specific for both N-Pyd and N-Dpd.

7. The method of claim 2, wherein said antibody is a polyclonal antibody.

8. The method of claim 7, wherein said polyclonal antibody is specific for N-Pyd.

9. The method of claim 1, wherein said sample is a serum or plasma sample.

10. The method of claim 9, wherein said obtaining includes the step of removing serum or plasma components having a molecular weight of greater than about 30 kDa, prior to said reacting.

11. The method of claim 9, wherein said obtaining includes the step of removing trichloroacetic acid-precipitatable serum or plasma sample components prior to said reacting.

12. The method of claim 1, wherein said antibody is attached to a solid-support, and said reacting is conducted in the presence of reporter-labeled pyridinium crosslinks effective to compete with such selected pyridinium crosslinks in the sample for binding to said antibody, and the amount of said immunocomplex formed is measured indirectly by measuring the amount of reporter-labeled pyridinium crosslinks bound to the solid-support.

13. The method of claim 1, wherein said antibody is reporter-labeled; a selected amount of said selected crosslinks is immobilized to a solid-support; and said reacting is conducted such that said immobilized crosslinks are effective to compete with such selected crosslinks from the sample for binding to said antibody, and the amount of said immunocomplex formed is measured indirectly by measuring the amount of reporter-labeled antibody bound to the solid-support.

14. A method of monitoring the status of a human cancer which involves, or which may progress to, a bone cancer condition, said method comprising reacting a non-hydrolyzed blood fluid sample from a human subject with an antibody which is specific for pyridinium crosslinks selected from the group consisting of native peptide-free pyridinoline (N-Pyd), native peptide-free deoxypyridinoline (N-Dpd), or both N-Pyd and N-Dpd, wherein said antibody is produced by immunizing an animal with hydrolyzed pyridinoline or hydrolyzed hydroxypyridinoline and said antibody has a ratio of reactivity toward said selected pyridinium crosslinks and urinay pyridinium peptides larger than 1,000 daltons in molecular weight, of greater than about 5:1, by said reacting, forming an immunocomplex between the antibody and such native peptide-free pyridinium crosslinks in the sample, measuring the amount of immunocomplex formed, and by said measuring, determining the concentration of such selected native peptide-free pyridinium crosslinks in the sample, wherein a determined concentration that is above (i) 5 nM N-Pyd, (ii) 1 nM N-Dpd, or (iii) 6 nM combined N-Pyd and N-Dpd indicates the presence of an above-normal level of collagen breakdown in the subject.

15. The method of claim 14, for use in monitoring treatment of such a cancer, wherein said identifying further includes determining changes in said selected crosslinks concentration during treatment of the cancer.

16. The method of claim 14, wherein the antibody is a monoclonal antibody having a binding constant for said selected crosslinks of at least $5 \times 10^7$/molar.

17. The method of claim 14, wherein the antibody is a polyclonal antibody having a binding constant for said selected crosslinks of at least $5 \times 10^7$/molar.

18. The method of claim 14, wherein said sample is a serum or plasma sample.

19. The method of claim 18, wherein said obtaining includes the step of removing serum or plasma components having a molecular weight of greater than about 30 kDa, prior to said reacting.

20. The method of claim 18, wherein said obtaining includes the step of removing trichloroacetic acid-precipitatable serum or plasma sample components prior to said reacting.

* * * * *